United States Patent [19]

Spann

[11] 4,108,170
[45] Aug. 22, 1978

[54] PATIENT SUPPORT STRAP

[76] Inventor: Donald C. Spann, 5 Fernwood Ct., Greenville, S.C. 29607

[21] Appl. No.: 780,762

[22] Filed: Mar. 24, 1977

[51] Int. Cl.² ............................................. A61F 13/00
[52] U.S. Cl. .................................................... 128/134
[58] Field of Search ................ 128/133, 134, DIG. 15

[56] References Cited

U.S. PATENT DOCUMENTS

| 2,404,505 | 7/1946 | Knecht | 128/134 |
| 4,036,220 | 7/1977 | Bellasalma | 128/DIG. 15 |

Primary Examiner—Lawrence W. Trapp
Attorney, Agent, or Firm—Bailey, Dority & Flint

[57] ABSTRACT

A support strap for use in supporting a patient as when seated to prevent slumping of the patient as when the patient becomes drowsy. An elongated strap is employed which is preferably constructed of polyurethane and the like which has a substantial thickness and a width several times that of the thickness in order to afford a degree of yieldability. The opening formed by the strap is deformable but the strap is of sufficient width to prevent the strap from twisting. Since the strap possesses a substantial cross-sectional area, yielding under limited force to a certain extent is permitted while further yielding will be arrested. Lengths of Velcro fastening members are provided on opposite sides adjacent the ends of the strap permitting fastening of the strap about the body and a supporting member with sufficient adjustability to accommodate various sizes of patients to a variety of positions.

1 Claim, 2 Drawing Figures

PATIENT SUPPORT STRAP

BACKGROUND OF THE INVENTION

Straps which have been utilized for supporting patients heretofore have been makeshift and generally consist of woven textile material which are narrow and afford little, if any stretchability. Prolonged use of such straps tend to cut off the circulation, particularly capillary blood flow.

It is an important object of this invention to provide a strap which is yieldable at the point of contact to conform to the body and the support as well as yieldable in length to a limited extent at which point yielding will become arrested due to the fact that the strap is incapable of further elongation and the application of substantially greater force will cause rupture of the strap. The strap affords a cushioning affect at a substantial area of contact conforming with the patient to prevent cutting off the circulation.

BRIEF DESCRIPTION OF THE INVENTION

It has been found that a strap for us for supporting a patient in seated position or to support the limbs of a patient and the like may be readily provided by utilizing an elongated strap constructed from a synthetic foam material, such as polyurethane. The strap has a substantially rectangular cross-section and a width sufficient to afford a cushioning effect and to prevent tearing of the strap material which is of a substantial width. The width of the strap is sufficient to afford a substantial area of cushioned contact with the patient and it has been found that about three inches of width is satisfactory in order to provide resistance to initial yielding in order to provide a cushioned support for the patient. A length of Velcro fastener hook tape is secured on one of the faces of the strap adjacent an end thereof, and a length of Velcro fastener loop tape is secured on the other face of the strap adjacent the other end thereof. It is important that the Velcro fasteners are of sufficient length to afford a desired adjustability to the strap.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
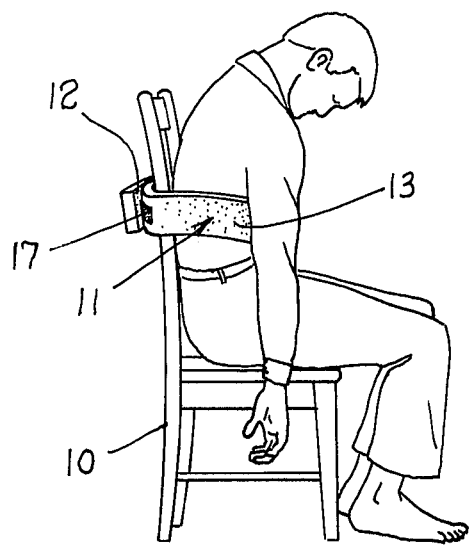
FIG. 1 is a perspective view illustrating a support strap constructed in accordance with the present invention supporting a seated patient.
Figure 2:
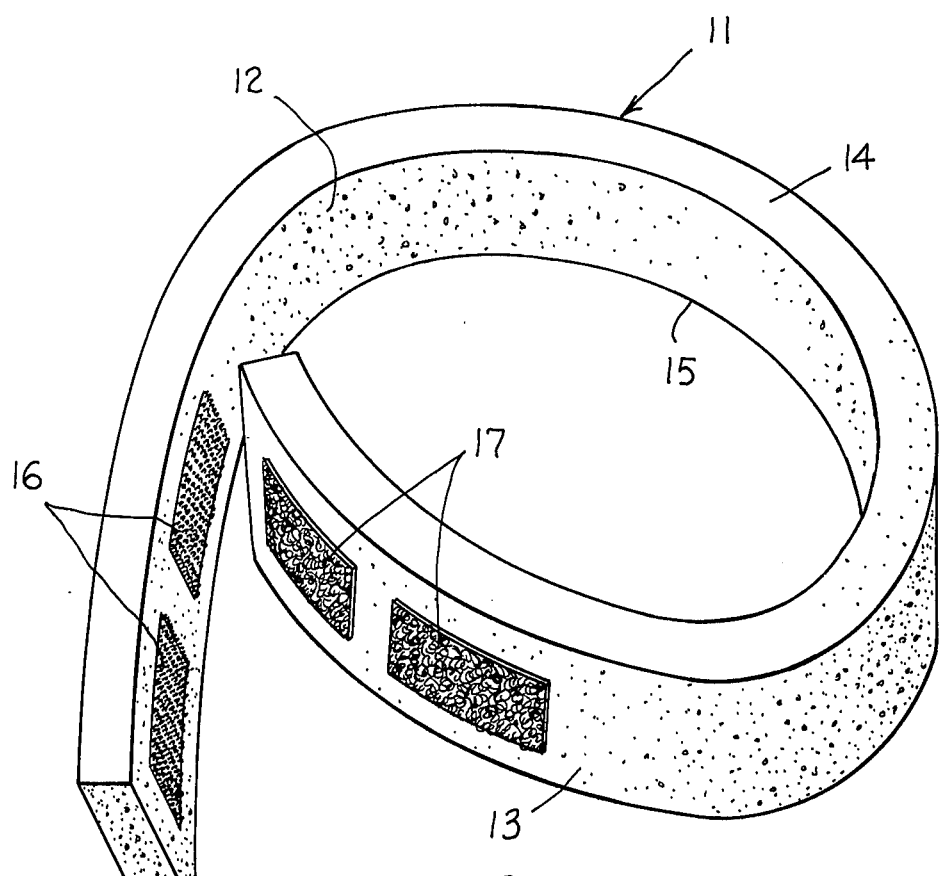
FIG. 2 is an enlarged perspective view further illustrating the support strap shown in FIG. 1.

The drawing illustrates a support strap for a seated patient to prevent slumping of the patient as when becoming drowsy or falling asleep. A straight chair is illustrated at 10, although the invention may be utilized in a variety of ways, such as with wheel chairs. If desired, the straps may be utilized to immobilize a limb which is in a sling by passing same about the body and the limb. The straps may be used in combination to form a sling or for securing any part of the body to another part or object.

An elongated strap broadly designated at 11, is constructed essentially of synthetic foam material. An open cell material such as polyurethane, is preferred but polystyrene and the like may also be employed. The strap has a substantially rectangular cross-section with opposed faces 12 and 13 of a width on the order of about three inches and opposed edges 14 and 15 of a thickness on the order of about one inch. These specific dimensions may vary widely so long as the approximate proportion and cross-sectional area is maintained to provide the desired yieldability and support strength without tearing. The length of the strap is of sufficient length to pass about a chair and the girth of the patient.

A length of Velcro fastener hook tape 16 is secured on one of the faces adjacent the other end of the strap. A length of Velcro fastener loop tape 17 is secured on the other of the faces adjacent the other end of the strap. Velcro brand tape fasteners are distributed by Smalley & Bates, Inc. 88 Park Avenue, Nutley, N.J. The Velcro fasteners are of sufficient length to afford adjustability to the support strap to accommodate a variety of patients and chairs. Thus, an extensive area of support contact with the patient is provided together with limited yieldability.

It is thus seen that an extremely versatile supporting and securing strap has been provided which adds significantly to the comfort and well-being of patients in a variety of situations. Due to the fact that patients secured by the strap are gently cushioned without loss of circulation, they may be left unattended freeing hospital personnel for other duties.

The support strap does not act to restrain the patient but does facilitate moving the patient in a wheelchair or for supporting a patient when seated at table. The strap is easily positioned by wrapping the safety strap about the patient's chest and chair back and making contact with the hooks and loops of the fastener tape. Since the strap is conformable to the body and does not bind, it is especially useful with female patients. While the strap may be autoclaved it is inexpensive and suited for one patient use for the duration of treatment.

While a preferred embodiment of the invention has been described using specific terms, such description is for illustrative purposes only, and it is to be understood that changes and variations may be made without departing from the spirit or scope of the following claims.

What is claimed is:

1. A support strap as for a seated patient to prevent slumping of the patient as when losing consciousness consisting essentially of:
   an elongated strap constructed of synthetic foam material;
   said strap being of substantially rectangular cross-section and having opposed faces of a width on the order of about three inches and opposed edges of a thickness on the order of about one inch;
   the length of said strap being sufficient to pass about a chair and the girth of the patient;
   a length of Velcro fastener hook tape secured on one of said faces adjacent an end of said strap;
   a length of Velcro fastener loop tape secured on the other of said faces adjacent the other end of said strap; and
   said Velcro fastener tapes being of sufficient length to afford adjustability to said support strap when joined to accommodate a variety of patients and chairs;
   whereby an extensive area of support contact with the patient is provided together with limited yieldability.

* * * * *